United States Patent [19]

Einset

[11] 4,294,252

[45] Oct. 13, 1981

[54] OSTOMY DEVICE

[76] Inventor: Eystein Einset, 1916 Sunset Dr., St. Joseph, Mich. 49085

[21] Appl. No.: 91,338

[22] Filed: Nov. 5, 1979

[51] Int. Cl.³ .............................................. A61F 5/44
[52] U.S. Cl. ................................................ 128/283
[58] Field of Search ............... 128/275, 283, 294, 295

[56] References Cited

U.S. PATENT DOCUMENTS

| | | |
|---|---|---|
| 310,210 | 1/1885 | Liedel . |
| 2,585,716 | 2/1952 | Zaetz . |
| 2,595,934 | 5/1952 | Ginsberg . |
| 2,638,898 | 5/1953 | Perry ................................ 128/283 |
| 2,721,553 | 10/1955 | Perry . |
| 2,796,063 | 6/1957 | Smelser ............................ 128/283 |
| 3,006,343 | 10/1961 | Baxter . |
| 3,039,464 | 6/1962 | Galindo . |
| 3,100,488 | 8/1963 | Orowan ............................ 128/283 |
| 3,398,744 | 8/1968 | Hooper . |
| 3,528,420 | 9/1970 | Nielsen . |
| 3,557,790 | 1/1971 | Hauser . |
| 3,736,934 | 6/1973 | Hennessy . |
| 3,865,109 | 2/1975 | Elmore et al. . |
| 3,869,762 | 3/1975 | Barrett et al. ...................... 128/283 |
| 3,948,256 | 4/1976 | Schneider ......................... 128/283 |

Primary Examiner—C. Fred Rosenbaum
Attorney, Agent, or Firm—Wegner, Stellman, McCord, Wood & Dalton

[57] ABSTRACT

An ostomy device for holding the neck of a drainage sleeve in operative association with a body opening such as for collecting fluids draining outwardly through the body opening. The device is formed as a one-piece gasket arranged to clamp the sleeve neck upon arrangement of different portions of the device in clamping association with an out-turned portion of the sleeve neck clamped therebetween. The device is arranged to be retained on the user's body by affixation of a belt or the like and includes structure for removable connection of the belt thereto.

11 Claims, 5 Drawing Figures

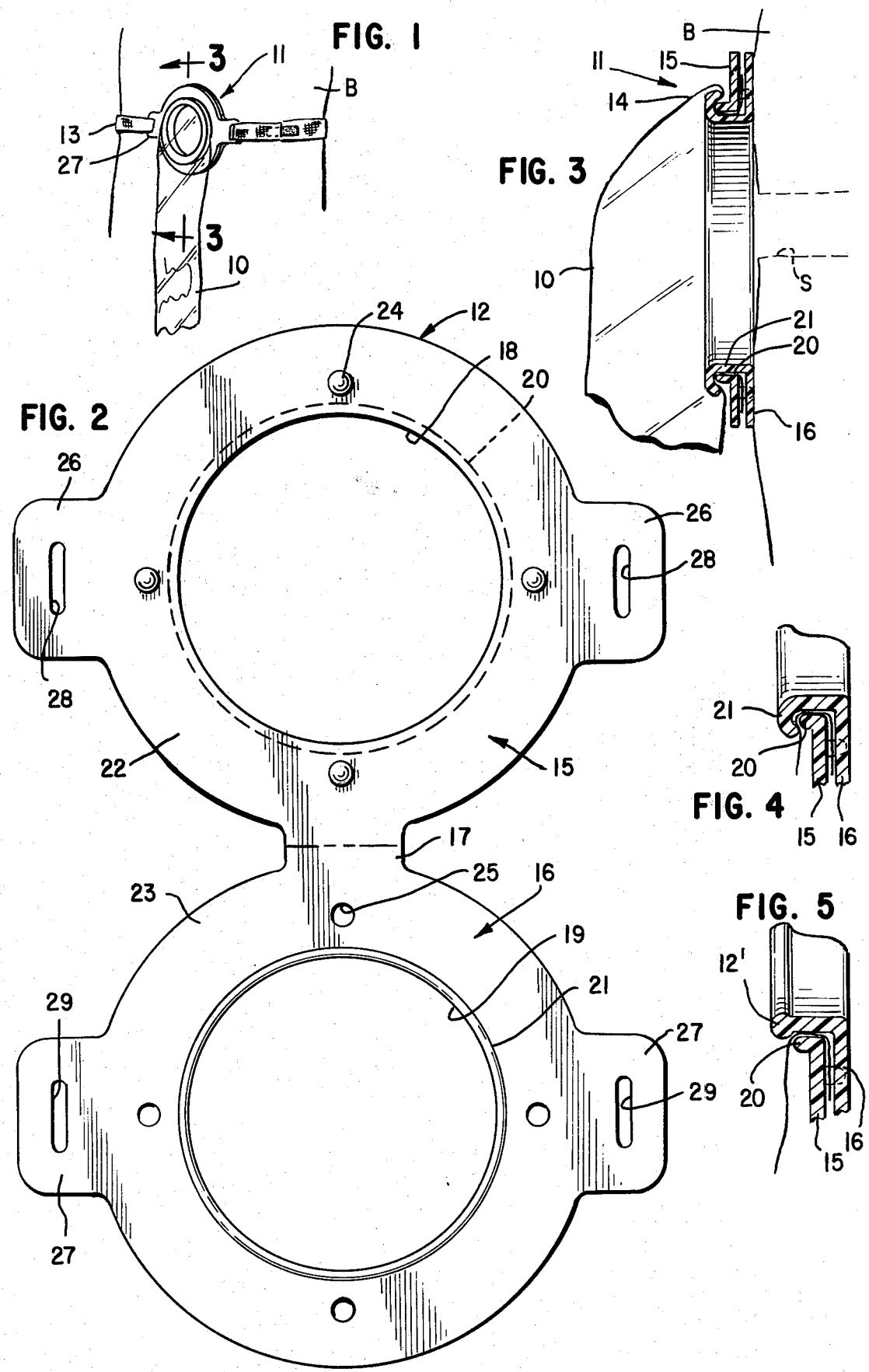

OSTOMY DEVICE

BACKGROUND OF THE INVENTION

1. Field of the Invention

This invention relates to ostomy devices and in particular to means for disposing the neck of a drainage sleeve in operative position to collect fluids draining from a body opening.

2. Description of the Prior Art

A number of devices have been developed for holding collecting bags and the like for a wide range of purposes including ostomy purposes wherein the bag is retained to receive fluids draining outwardly from a body opening. Such devices are utilized, for example, in connection with colostomies and ileostomies.

Such devices conventionally utilize disposable collecting bags which illustratively may be formed of flexible plastic material. Such plastic material may be relatively slippery and it is important to provide a firm, positive retention of the neck of the bag in association with the user's body to receive the fluids draining through the body opening.

An early form of bag holder, such as for holding grain sacks during the filling thereof, is illustrated in U.S. Pat. No. 310,210, of Ludwig Liedel. As shown therein, the bag holder includes a standard, a foot piece, frame pieces having slots, and a frame having lugs, a catch and rims.

Saul P. Zaetz shows, in U.S. Pat. No. 2,585,716, a drainage receptor more specifically for use in an ostomy application wherein a bag neck is secured to receive body fluids. The bag neck is held to a post portion of the connector by a ring spring urging the bag neck into an annular groove in the post portion.

Nathan Ginsburg shows, in U.S. Pat. No. 2,595,934, a colostomy apparatus wherein the bag is clamped to a support plate by an elastic band or metallic resilient clamp illustrated in FIG. 4 of the patent.

Merle Perry, in U.S. Pat. No. 2,721,553, shows a stoma receiver including a pair of bag clamping, mounting and supporting rings having separable, substantially concentric cylindrical segments sealingly receiving the mouth portion of the bag between the segments to grip the mouth portion and hold it in an open position while providing an annular reinforced opening while cooperating with a foundation ring mounted on the outside thereof.

Thomas R. Baxter shows an ostomy device for supporting a collecting bag, in U.S. Pat. No. 3,006,343, including an annulus which is pliable so as to be conformable to the abdominal contours of the user when clamped thereto and which, after a period of usage, takes a physical set in the shape dictated by such contours. A plurality of turns of the mouth of the bag may be wrapped around the ring structure in securing the bag thereto.

In U.S. Pat. No. 3,039,464, Edmund N. Galindo shows an ileostomy appliance wherein a pair of wedged rings secure the bag mouth therebetween. The outer ring may be pried from the inner ring which may be retained in position on the wearer's body.

Edwin A. Hooper shows, in U.S. Pat. No. 3,398,744, a colostomy appliance wherein the bag mouth is tightly gathered around the neck of one portion of the connector. A sealing and retaining unit encircles the mouth portion of the bag and neck and is manually applicable and removable. This portion includes a cleat for connection of a belt thereto.

In U.S. Pat. No. 3,528,420, John Henning Schlatt Nielsen shows a colostomy appliance wherein the edges of an opening in one side of the bag are secured to an outer flange of a retaining ring having an axially extending annular engaging flange extending into the bag. The connecting member has, at one end, a carrying flange attached to an adhesive flange adapted to be attached to the wearer's body.

Raul C. Hauser discloses, in U.S. Pat. No. 3,557,790, an ostomy appliance consisting of an outer plate which fits over a disposable expanded polystyrene disc. The disc is held against the wearer's skin surrounding a stoma and the pouch is clamped between the plate and the disc. The securing belt is connected to the plate.

A surgical drainage appliance is illustrated in U.S. Pat. No. 3,736,934 of Alexander J. Hennessy, with a connector structure thereof adapted to clamp the mouth of the collecting bag between annular surfaces of cooperating ring members.

In U.S. Pat. No. 3,865,109, Austin E. Elmore et al show a colostomy pouch having venting means. The mouth of the collecting bag is clamped between a belt-plate. The pouch is secured to the belt-plate by any suitable means, such as adhesive.

SUMMARY OF THE INVENTION

The present invention comprehends an ostomy device having an improved means for retaining the collecting bag in association with the user's body.

More specifically, the invention comprehends such an ostomy device having a drainage sleeve provided with a flexible connecting neck defining an inlet opening having improved retaining means for use in retaining the sleeve neck to a user's body in alignment with a stoma therein for collecting material draining outwardly through the stoma, the improved retaining means including a one-piece gasket having a first inner clamp half provided with a first drain opening, a second outer clamp half provided with a second drain opening, a hinge connecting the clamp halves for selective spaced disposition and facially overlying clamping disposition with the drain openings aligned, cooperating means on the clamp halves for sealingly securing the sleeve neck between the clamp halves in the clamping disposition with the neck passed through the second drain opening of the outer clamp half and outturned between the clamp halves with the inlet opening aligned with the first drain opening of the inner clamp half, and means for releasably securing the clamp halves in the clamping disposition.

The securing means for securing the clamp halves in clamping association with the sleeve neck may define cooperating interlock means. The interlock means may comprise an annular projection on one of the clamp halves interlocked with an annular shoulder on the other clamp halves with the sleeve neck serpentinely clamped therebetween.

The device may further include holding means for releasably holding the assembled gasket and drainage sleeve in position on the user's body wherein the holding means further serves to retain the clamp halves in the clamping association. More specifically, the holding means may include attachment openings in each of the clamp halves which are aligned when the clamp halves are brought to the clamping disposition, permitting the belt means to extend through the aligned openings and thereby secure the belt to the device and retain the clamp halves in juxtaposed clamping disposition.

The one-piece gasket may be formed with the clamp halves extending generally coplanarly and with the hinge comprising a living hinge permitting the clamp halves to be repositioned approximately 180° from the coplanar arrangement.

The ostomy device of the present invention is extremely simple and economical of construction while yet providing the highly improved low cost, effectively positive clamping structure for retaining the ostomy sleeve in collecting disposition on the user's body.

BRIEF DESCRIPTION OF THE DRAWING

Other features and advantages of the invention will be apparent from the following description taken in connection with the accompanying drawing wherein:

FIG. 1 is a fragmentary perspective view of a wearer utilizing an ostomy device embodying the invention;

FIG. 2 is an enlarged plan view of the gasket as manufactured;

FIG. 3 is a fragmentary enlarged section taken substantially along the line 3—3 of FIG. 1 illustrating the connection of the sleeve neck to the gasket;

FIG. 4 is a fragmentary further enlarged section illustrating a portion of the structure of FIG. 3; and FIG. 5 is a fragmentary schematic illustration of a modified form of interlock means of the gasket.

DESCRIPTION OF THE PREFERRED EMBODIMENTS

In the exemplary embodiment of the invention as shown in FIG. 1 of the drawing, a collecting sleeve 10 is held in operative association with a person's body B so as to receive fluids draining from a stoma therein. The sleeve is removably connected to a retaining device generally designated 11 which may include a connecting gasket generally designated 12, and a holding means generally designated 13 illustratively comprising a removable belt for retaining the device in operative position on the user's body.

More specifically, the sleeve may comprise a plastic bag adapted to hold the body fluids. The bag may define a neck, or mouth, portion 14 arranged to be connected to the gasket for holding the assembly in place on the user's body, as shown in FIG. 1.

Referring more specifically to FIG. 2, gasket 12 is shown to comprise a pair of clamp halves 15 and 16, respectively. As seen in FIG. 2, the clamp halves are defined as portions of a one-piece gasket 12 being hingedly connected by a lifting hinge portion 17.

The clamp halves may effectively define annular structures wherein clamp half 15 has a central opening 18 and clamp half 16 has a central opening 19. Opening 18 may be defined by a turned annular flange 20. Opening 19 may be defined by an outturned flange 21. Flange 21 has a size and is arranged on clamp half 16 so as to pass through opening 18 when the clamp half 16 is swung on hinge 17 180° from the coplanar relationship illustrated in FIG. 2, such as to bring the flange 21 firstly upwardly and then downwardly into the plane of the paper, as seen in FIG. 2.

As seen in FIG. 2, the rear face 22 of clamp half 15 and the front face 23 of clamp half 16 are substantially planar so as to be brought into facial juxtaposition with each other when clamp half 16 is so swung, as indicated above.

The clamp halves are further provided with second interlocking means which may be provided in the form of a plurality of rearwardly extending projections 24 on the rear face 22 of clamp half 15 and cooperating openings 25 in the clamp half 16. The projections 24 are located and sized to be fitted into the openings 25 when the clamp half 16 is brought into facial juxtaposition with the rear face 22 of clamp half 15.

As further illustrated in FIG. 2, each of the clamp halves is provided with diametrically opposed tab portions, including tab portions 26 of clamp half 15 and tab portions 27 of clamp half 16. Tabs 26 are provided with slots 28 and tabs 27 are provided with similar slots 29, which are brought into overlying congruency when the clamp half 16 is swung into facial engagement with the rear surface 22 of clamp half 15.

The gasket 12 may be formed of a suitable synthetic resin and, thus, may be economically formed as a one-piece molded element.

The retention of the bag mouth 14 in positive clamped association with gasket 12 is effected by simply bringing the bag mouth rearwardly through the opening 18, as seen in FIG. 2, and flaring the bag mouth outwardly to overlie the rear surface 22 thereof and the projections 24. Clamp half 16 is then swung, as discussed above, so as to bring the outturned flange portion 21 thereof into the outwardly flared bag mouth and through the opening 18 in clamp half 15 to snap past the front edge of flange 20 and thereby clamp the bag mouth 14 positively between the flanges 20 and 21 serpentinely, as illustrated in FIG. 3. The serpentine arrangement of the bag mouth 14 in the clamped association with flanges 20 and 21 effectively secures the bag sealingly to the gasket. In addition, as shown in FIG. 3, the projections 24 extend through the turned bag mouth portion into the openings 25 of clamp half 16 to provide further positive securing of the bag to the connecting gasket. The snapped interlocked association of flange 21 with flange 20 provides positive retention of the clamp halves in the clamping disposition, thereby effectively precluding slipping of the bag mouth 14 from the connector.

Further, retention of the clamp halves in the swung facially juxtaposed disposition of FIG. 3 is effected by the extension of the holding belt connecting portions 27 through the aligned openings 28 and 29, thereby further effectively preventing separation of the clamp halves in use as when worn on the user's body, as illustrated in FIG. 1.

Referring to FIG. 5, a modified form of interlocking flange 121 may be provided on the clamp half 16 for cooperating with the rear turned flange 20 of clamp half 15. As shown in FIG. 5, the flange 121 may comprise a beaded flange in lieu of the rolled-over turned flange 21. As will be obvious to those skilled in the art, other configurations of the interlocking flanges may be utilized within the scope of the invention. Similarly, other configurations of the cooperating projections 24 and openings 25 may be utilized within the scope of the invention.

As will be further obvious to those skilled in the art, the sleeve-holding device may be utilized in many other applications as well as the ostomy application illustratively disclosed. The device is advantageously adapted for use in supporting plastic sleeves or bags which are relatively slippery in providing the plurality of interlocking and holding structures in cooperation with the clamping action of the clamp halves. The automatic alignment of the interlocking flange configurations permits a facilitated, rapid connection of the bag mouth, or sleeve neck, to the attaching gasket and effectively assures a positive, secured connection thereof to the gasket.

The foregoing disclosure of specific embodiments is illustrative of the broad inventive concepts comprehended by the invention.

I claim:

1. In an ostomy device having a drainage sleeve provided with a flexible connecting neck defining an inlet opening, improved retaining means for use in retaining the sleeve neck to a user's body in alignment with a stoma therein for collecting material draining outwardly through the stoma, said retaining means comprising:

a one-piece gasket having a first inner clamp half provided with a first drain opening, a second outer clamp half provided with a second drain opening, a hinge comprising portions of said clamp halves connecting the clamp halves for selective spaced disposition and facially overlying clamping disposition with said drain openings aligned, cooperating means on said clamp halves for sealingly securing said sleeve neck between said clamp halves in said clamping disposition with said neck passed through said second drain opening of the outer clamp half and outturned between said clamp halves with said inlet opening aligned with said first drain opening of the inner clamp half, and at least two different types of releasable interlock means for releasably interlocking said clamp halves in said clamping disposition; and means for preventing disengagement of said interlock means when the device is being retained to the user's body.

2. The ostomy device of claim 1 wherein said interlock means includes means acting between said clamp halves and engaging said outturned neck for effectively positively securing said neck between said clamp halves.

3. The ostomy device of claim 1 wherein said interlock means includes a projection on one of said clamp halves and a mounting recess on the other of said clamp halves.

4. The ostomy device of claim 1 wherein said interlock means includes a projection on one of said clamp halves at the edge of the drain opening thereof extending into the drain opening of the other clamp half when the clamp halves are in said clamping disposition.

5. The ostomy device of claim 1 wherein said interlock means includes a turned projection on one of said clamp halves at the edge of the drain opening thereof extending into the drain opening of the other clamp half when the clamp halves are in said clamping disposition and snapped laterally outwardly to overlie the edge of the other of said clamp halves defining the drain opening thereof.

6. The ostomy device of claim 1 wherein said interlock means includes a turned projection on one of said clamp halves at the edge of the drain opening thereof extending into the drain opening of the other clamp half when the clamp halves are in said clamping disposition and snapped laterally outwardly to overlie the edge of the other of said clamp halves defining the drain opening thereof, said edge of the other clamp half defining a projection extending away from said one clamp half.

7. The ostomy device of claim 1 wherein said interlock means includes a turned projection on one of said clamp halves at the edge of the drain opening thereof extending into the drain opening of the other clamp half when the clamp halves are in said clamping disposition and snapped laterally outwardly to overlie the edge of the other of said clamp halves defining the drain opening thereof, said edge of the other clamp half defining a projection extending away from said one clamp half and said turned projection of the one clamp half including a distal portion turned back toward said one clamp half, said sleeve neck being captured between said projections for effective positive locked retention therebetween.

8. The ostomy device of claim 1 wherein said means for preventing disengagement of the interlock means comprises holding means for releasably holding the assembled gasket with said drainage sleeve sealingly mounted thereto in position on the user's body to collect in said sleeve material passed outwardly through said stoma, said holding means defining means for holding the first clamp half against the user's body surrounding said stoma.

9. The ostomy device of claim 8 wherein said holding means includes belt attachment openings in each of said clamp halves which are aligned when the clamp halves are in the clamping disposition, and belt means including connecting portions extended through said aligned openings.

10. The ostomy device of claim 8 wherein said holding means further defines means looped through said clamp halves for retaining said clamp halves in the clamping disposition.

11. The ostomy device of claim 8 wherein said holding means comprise means spaced at opposite sides of said hinge.

* * * * *